(12) United States Patent
Van Saarloos (10) Patent No.: US 7,221,494 B2
(45) Date of Patent: May 22, 2007

(54) SCANNING DEVICE AND METHOD OF SCANNING AN OPTICAL BEAM OVER A SURFACE

(75) Inventor: Paul Phillip Van Saarloos, Gwelup (AU)

(73) Assignee: CLVR Pty Ltd., Balcatta (AU)

( * ) Notice: Subject to any disclaimer, the term of this patent is extended or adjusted under 35 U.S.C. 154(b) by 291 days.

(21) Appl. No.: 10/519,382

(22) PCT Filed: Jun. 27, 2003

(86) PCT No.: PCT/AU03/00814

§ 371 (c)(1),
(2), (4) Date: Dec. 27, 2004

(87) PCT Pub. No.: WO2004/003625

PCT Pub. Date: Jan. 8, 2004

(65) Prior Publication Data

US 2005/0237590 A1    Oct. 27, 2005

(30) Foreign Application Priority Data

Jun. 28, 2002    (AU) ..................................... PS3261

(51) Int. Cl.
*G02B 26/08*    (2006.01)
(52) U.S. Cl. .................................................... 359/225

(58) Field of Classification Search ......... 359/223–226
See application file for complete search history.

(56) References Cited

U.S. PATENT DOCUMENTS 6,166,841 A    12/2000    Melville

FOREIGN PATENT DOCUMENTS

| GB | 2241592 A | 9/1991 |
|----|-----------|--------|
| JP | 2001-179180 A | 7/2001 |
| SU | 1778738 A | 11/1992 |
| WO | WO 02/46819 A | 6/2002 |

*Primary Examiner*—Euncha P. Cherry
(74) *Attorney, Agent, or Firm*—Foley & Lardner LLP (57) ABSTRACT

An optical scanning device (1) to scan an optical beam over a surface (S). The optical scanning device (1) uses a piezoelectric actuator (10) acting on a platform (2) that carries a mirror (4) to pivot the platform (2) about a pivot (8). Voltage is applied to the piezoelectric actuator (10) to pivot the platform (2) about the pivot (8). Changes in the applied voltage result in the angle at which the beam is reflected by the mirror (4) being altered. In this way, the reflected beam (R) can be scanned to different locations on the surface (S). Providing two such optical scanning devices (1a, 1b) or using two piezoelectric actuators (10aa, 10bb) acting on a single platform (2) enables two dimensional scanning of the surface (S) by the optical scanning device/s (1,1a, 1b). The optical scanning device (1) of the present invention may be used in refractive eye surgery laser apparatus.

45 Claims, 5 Drawing Sheets

SCANNING DEVICE AND METHOD OF SCANNING AN OPTICAL BEAM OVER A SURFACE

FIELD OF THE INVENTION

The present invention relates to an optical scanning device, a laser apparatus incorporating such an optical scanning device and a method of scanning an optical beam over a surface to perform material processing of the surface.

The applications of the present invention include, for example, surgical and medical applications, such as operations for correcting refractive errors of the eye by photorefractive keratectomy (PRK) or laser in-situ keratomileusis (LASIK). The present invention also has industrial applications for material processing. Material processing examples of industrial applications of the present invention include photolithography in microchip manufacture and glass marking.

BACKGROUND OF THE INVENTION

The specification refers to and describes content of U.S. Pat. Nos. 5,520,679, 6,339,278, 6,339,470 and 6,342,751. However, neither the disclosures in those US patents nor the description contained herein of content of those US patents is to be taken as forming part of the common general knowledge solely by virtue of the inclusion herein of the reference to and description of content of those US patents. Furthermore, this specification describes aspects of prior art optical scanning systems. However, neither such aspects of prior art optical scanning systems nor the description contained herein of such aspects of prior art optical scanning systems is to be taken as forming part of the common general knowledge solely by virtue of the inclusion herein of reference to and description of such aspects of prior art optical scanning systems.

A wide range of lasers are suitable for the above applications, including: excimer lasers, Nd:YAG, Nd:YLF, Er:YAG, Nd:KGW, Carbon Monoxide, and Carbon Dioxide lasers. The wavelengths produced by these lasers range from deep in the ultra-violet (UV) to long infra-red (IR) wavelengths.

A feature that is often common among the use of these lasers for material processing is the need to move the laser beam relative to the material surface being processed. When the material is not deliberately being moved and the laser beam is being directed to carry out the processing, the movement of the laser beam is often performed by galvanometer or motor driven mirrors and lenses.

In the field of treating refractive errors by laser ablation, J. T. Lin (U.S. Pat. No. 5,520,679) proposed using galvanometer scanners to control a low energy laser beam into an overlapping pattern of adjacent pulses to produce the desired change in the corneal surface. U.S. Pat. No. 5,520,679 states that this allows a smaller, lower cost laser to be used for this procedure. U.S. Pat. No. 5,520,679 also states other advantages, including a reduced need for a homogenous beam and better flexibility in design of the treatment.

Galvanometer scanning excimer lasers are currently one of the most common means for correcting refractive errors using the LASIK surgical procedure.

Although galvanometer scanners have been very successful in scanning lasers for reshaping corneal tissue and a large range of other applications, they do have some disadvantages. They have a trade-off between the size and weight of the mirror being tilted and the speed by which the galvanometer can adjust its position. Sometimes this results in mirrors that are not large enough for the optical system or using mirrors that are too thin to maintain their required flatness during the scanning process. Galvanometer scanners also have limited accuracy when the desired scan angle is small (less than 3 degrees).

The galvanometer scanners used in refractive lasers generally work well at the pulse repetition rates currently used, i.e. 200 Hz or below. However, this assumes that the eye is not moving. Tracking the eye has now become an important part of producing good results for refractive surgery. Between each pulse the position of the eye is measured and then the scanner position adjusted to compensate for any eye movements before the eye moves again. This means that the scanner must be capable of moving much faster than when the laser was operating without an eye tracker. These faster response requirements from the scanner go beyond the response capabilities of galvanometers. This becomes even more of a problem when the demands of customised surgery require smaller spot sizes to ablate with higher precision and subsequently much higher pulse repetition rates. Galvanometric scanners would not have adequate response for such a laser system.

A problem that sometimes occurs in galvanometric scanners if the eye moves slightly up and down, getting closer or further away from the laser, is that each pulse may not hit the eye in the correct position. Because of the scan angle, if the eye is too close to the laser system then the pulses over-lap more than intended and the total area exposed to the laser is less than intended. If the eye is too far from the laser the opposite occurs. In either case, the result of the surgery is degraded.

An alternative drive mechanism to a galvanometer drive mechanism is a piezoelectric drive.

Piezoelectric drives have the advantages of having potentially infinite precision and are capable of generating extremely high forces, so could drive a large mirror very fast. However, piezoelectric drives also have a number of significant disadvantages, and although they have been used to scan laser beams, they have not been generally accepted for this type of application because of these disadvantages.

The main disadvantage of piezoelectric drive systems is their very limited range of movement. They are therefore not considered to be a potential means of scanning in applications currently performed by galvanometer scanners. One method that has been used to amplify the range of piezoelectric scanning is to have the piezoelectric crystals push or pull on the end of a metal plate. The metal plate bends and deflects a mirror further than the same piezo would move the mirror if applied behind the edge of the mirror. A device based on this technique is described by Takeuchi et al in U.S. Pat. No. 6,342,751. However, this type of technique creates a non-linear beam deflection and loses much of the potential accuracy of a piezoelectric drive mechanism, and still has a much smaller range of scanning than galvanometer scanners. These types of techniques also suffer from reduced response time, stiffness and have a significantly smaller force/load capability.

The second significant problem with piezoelectric drive systems, or actuators, is that they have significant hysteresis. This is normally in the order of 10% to 15% of the range of the movement. This hysteresis is another key reason why piezoelectric driven scanners are currently not used in applications requiring fast complex scan pattens, such as laser systems for refractive surgery. This hysteresis can be corrected by operating the piezoelectric system in a closed loop fashion. This requires a sensor to measure the movement of the system and then a controller that adjusts the voltage to the piezoelectric actuator so that it moves to the desired position. The problem with this is that it significantly reduces the response of the system, and its accuracy is reduced to the accuracy of the sensor. In an application in which tolerances are critical, such as refractive surgery, the hysteresis induced error can be so large that the piezoelectric signal and position sensor signal cannot be compared to check the system is operating correctly. So to achieve a redundant check of scanning performance a second position sensor would need to be used.

Papademetriou, et al in U.S. Pat. No. 6,339,470 describes means for scanning lasers across optical fibres. This US patent also describes use of a piezoelectric stack to adjust the angle of a mirror. However, this description complains of the lack of range of such a scanning mechanism as special effort is required to scan the laser across the entrance of a single optical fibre. The main scanning mechanism used in the device described in this US patent relies on acousto-optic deflection of the laser beam, where that scan range must cover more than one optic fibre (which is smaller than the range across an eye). Acousto-optic scanners are relatively complex, have high optical losses and are not suitable for many of the wavelengths used for material processing applications.

The background description in U.S. Pat. No. 6,339,278 (Shinohara, et al) describes conventional inclination optical scanners and lists galvanometers, stepper motors and other mechanisms as examples but not piezoelectric mechanisms. However, the invention described in this US patent does use a piezoelectric device, but it is used as a mechanical oscillator to drive an ultrasonic motor that deflects the laser beam.

DISCLOSURE OF THE INVENTION

In accordance with a first aspect of the present invention, there is provided an optical scanning device comprising:
  a platform,
  a mirror provided on said platform to reflect an optical beam incident on said mirror,
  a pivot about which said platform is able to pivot,
  at least first piezoelectric actuator means to act on said platform to pivot said platform about said pivot in a first direction,
  at least first resilient means to bias said platform about said pivot in a second direction opposed to said first direction,
  wherein said first piezoelectric actuator means acts on said platform at a location in proximity to said pivot, to pivot said platform such that the angle at which said beam is reflected by said mirror is altered to alter the path of the reflected beam to thereby scan the reflected beam in a first plane over a surface.

In an alternative form, the optical scanning device further comprises:
  second piezoelectric actuator means to pivot said platform about said pivot in a third direction,
  second resilient means to bias said platform about said pivot in a fourth direction opposed to said third direction, and
  wherein said second piezoelectric actuator means acts on said platform at a location in proximity to said pivot, to pivot said platform such that the angle at which said beam is reflected by said mirror is altered to alter the path of the reflected beam to thereby scan the reflected beam in a second plane over the surface, such that said reflected beam is scannable over said surface in two dimensions.

In accordance with a second aspect of the present invention there is provided an optical scanning apparatus comprising:
  a first optical scanning device, and
  a second optical scanning device,
  said first optical scanning device comprising:
  a first platform
  a first mirror provided on said first platform to reflect an optical beam incident on said first mirror,
  a first pivot about which said first platform is able to pivot,
  first piezoelectric actuator means to act on said first platform to pivot said first platform about said first pivot in a first direction, and
  first resilient means to bias said first platform about said first pivot in a second direction opposed to said first direction, and
  said second optical scanning device comprising
  a second platform
  a second mirror provided on said second platform to reflect the optical beam incident on said second mirror,
  a second pivot about which said second platform is able to pivot,
  second piezoelectric actuator means to act on said second platform to pivot said second platform about said second pivot in a third direction, and
  second resilient means to bias said second platform about said second pivot in a fourth direction opposed to said third direction,
  wherein said first piezoelectric actuator means acts on said first platform at a location in proximity to said first pivot to pivot said first platform such that the angle at which said beam is reflected by said first mirror is altered to alter the path of the reflected beam to thereby scan the reflected beam in a first plane, and said second optical scanning device is arranged such that said second mirror receives said beam reflected by said first mirror and said second piezoelectric actuator means acts on said second platform at a location in proximity to said second pivot to pivot said second platform such that the angle at which said beam is reflected by said second mirror is altered to alter the path of the reflected beam to thereby scan the reflected beam in a second plane, such that said reflected beam is scannable over said surface in two dimensions.

In accordance with a third aspect of the present invention there is provided a laser apparatus comprising:
  a laser to emit an optical beam,
  a first optical scanning device, and
  a second optical scanning device,
  said first optical scanning device comprising
  a first platform
  a first mirror provided on said first platform to reflect an optical beam incident on said first mirror,
  a first pivot about which said first platform is able to pivot,
  first piezoelectric actuator means to act on said first platform to pivot said first platform about said first pivot in a first direction, and
  first resilient means to bias said first platform about said first pivot in a second direction opposed to said first direction, and
  said second optical scanning device comprising
  a second platform
  a second mirror provided on said second platform to reflect the optical beam incident on said second mirror,
  a second pivot about which said second platform is able to pivot, second piezoelectric actuator means to act on said second platform to pivot said second platform about said second pivot in a third direction, and second resilient means to bias said second platform about said second pivot in a fourth direction opposed to said third direction, wherein said first piezoelectric actuator means acts on said first platform at a location in proximity to said first pivot to pivot said first platform such that the angle at which said beam is reflected by said first mirror is altered to alter the path of the reflected beam to thereby scan the reflected beam in a first plane, and said second optical scanning device is arranged such that said second mirror receives said beam reflected by said first mirror and said second piezoelectric actuator means acts on said second platform at a location in proximity to said second pivot to pivot said second platform such that the angle at which said beam is reflected by said second mirror is altered to alter the path of the reflected beam to thereby scan the reflected beam in a second plane, such that said reflected beam is scannable over said surface in two dimensions to thereby scan the reflected beam over a surface to perform material processing of said surface by the reflected beam and the optical path of the reflected beam from said second optical scanning device to the said surface is substantially one metre or more in length.

Preferably, a third mirror is provided to reflect the reflected beam reflected by said mirror of said second optical scanning device prior to said reflected beam being reflected to said surface.

More preferably, a fourth mirror is provided to receive the reflected beam from said third mirror and said fourth mirror reflects said reflected beam to said surface.

In accordance with a fourth aspect of the present invention there is provided a laser apparatus comprising:
a laser to emit an optical beam, and
an optical scanning device comprising
a platform,
a mirror provided on said platform to reflect a said optical beam incident on said mirror,
a pivot about which said platform is able to pivot,
first piezoelectric actuator means to act on said platform to pivot said platform about said pivot in a first direction,
first resilient means to bias said platform about said pivot in a second direction opposed to said first direction,
second piezoelectric actuator means to act on said platform to pivot said platform about said pivot in a third direction,
second resilient means to bias said platform about said pivot in a fourth direction opposed to said third direction, wherein said first piezoelectric actuator means acts on said platform at a location in proximity to said pivot, to pivot said platform such that the angle at which said beam is reflected by said mirror is altered to alter the path of the reflected beam to thereby scan the reflected beam in a first plane and said second piezoelectric actuator means acts on said platform at a location in proximity to said pivot, to pivot said platform such that angle at which said beam is reflected by said mirror is altered to alter the path of the reflected beam to thereby scan the reflected beam in a second plane, said first plane and said second plane being substantially mutually orthogonal, to thereby scan the reflected beam over a surface to perform material processing of said surface by the reflected beam and the optical path of the reflected beam from said optical scanning device to said surface is substantially one metre or more in length.

Preferably, a second mirror is provided to reflect the reflected beam reflected by said mirror of said optical scanning device prior to said reflected beam being reflected to said surface.

More preferably, a third mirror is provided to receive the reflected beam from said second mirror and said third mirror reflects said beam to said surface.

Preferably, the first plane and the second plane are substantially mutually orthogonal.

Preferably, said first piezoelectric actuator means acts on said platform to push said platform and said first resilient means is compressively or expandably resilient.

Alternatively, said first piezoelectric actuator means acts on said platform to pull said platform and said first resilient means is compressively or expandibly resilient.

Preferably, said second piezoelectric actuator means acts on said platform to push said platform and said second resilient means is compressively or expandably resilient.

Alternatively, said second piezoelectric actuator means acts on said platform to pull said platform and said second resilient means is compressively or expandably resilient.

The optical beam may be a laser beam.

The laser apparatus may be a refractive eye surgery laser apparatus, in which case the surface on which the material processing is performed by the reflected beam is the eye of a patient on which the refractive surgery is performed by the reflected beam.

However, the laser apparatus may also be used in other medical applications, in which case the surface on which the material processing is performed by the reflected beam is (human or animal) tissue. Another use of the laser apparatus is as an industrial laser.

In accordance with a fifth aspect of the present invention there is provided a method of scanning an optical beam, in at least a first plane, over a surface using at least one optical scanning device as hereinbefore described comprising determining a required location for an optical beam to be incident on said surface, determining whether a positive or negative change to the voltage applied to a said piezoelectric actuator means is required to pivot said platform to a required position corresponding to the said required location, comparing the existing position of said platform and the voltage applied to said piezoelectric actuator means with the required position of said platform, calculating the required voltage to be applied to said piezoelectric actuator means corresponding to the required position of said platform, applying the said required voltage to said piezoelectric actuator means to move the platform to said required position such that the optical beam is incident on said surface at the said required location.

Preferably, said required position of said platform and the corresponding required voltage to be applied to said piezoelectric actuator means are recorded for use in determining the voltage to be applied to said piezoelectric actuator means for the next location at which said optical beam is to be incident on said surface In one preferred embodiment of the method of scanning an optical beam, an optical scanning device in accordance with the alternative form of the optical scanning device in accordance with the first aspect of the present invention is provided to scan the optical beam in two planes over said surface, wherein the steps of the method as hereinbefore described are carried out on each of the first piezoelectric actuator means and the second piezoelectric actuator means to pivot said platform to the required position for the optical beam to be incident on said surface at said required location.

In an alternative preferred embodiment of the method of scanning an optical beam, an optical scanning apparatus in accordance with the second aspect of the present invention is provided to scan the optical beam in two planes over the surface, wherein the steps of the method hereinbefore described in accordance with the fifth aspect of the present invention are carried out on the first piezoelectric actuator means of the first optical scanning device and the second piezoelectric actuator means of the second optical scanning device to pivot the respective platform of said first optical scanning device and said second optical scanning device to the required position, respectively, for the optical beam to be incident on said surface at the required location.

The method hereinbefore described may be used in applications such as performing refractive eye surgery on a patient, in which case the surface over which the optical beam is scanned is the eye of the patient.

The method may also be used in other medical applications, in which case the surface over which the optical beam is scanned is (human or animal) tissue.

The method may also be used in material processing applications in industry.

BRIEF DESCRIPTION OF THE DRAWINGS

The present invention will now be described, by way of example, with reference to the accompanying drawings, in which:

FIG. 1b is a cross section view taken along the line A—A in FIG. 1a;

BEST MODE OF CARRYING OUT THE INVENTION

Figure 1A:
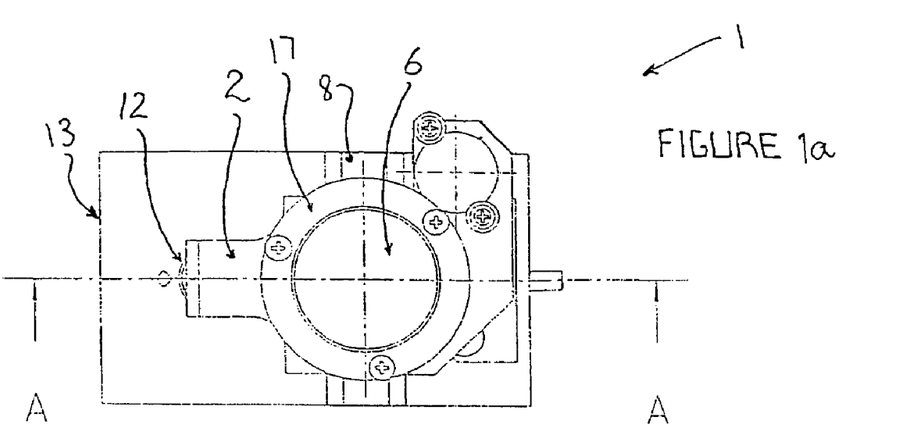
FIG. 1a is a plan view of a first embodiment of an optical scanning device in accordance with an aspect of the present invention.
Figure 1B:
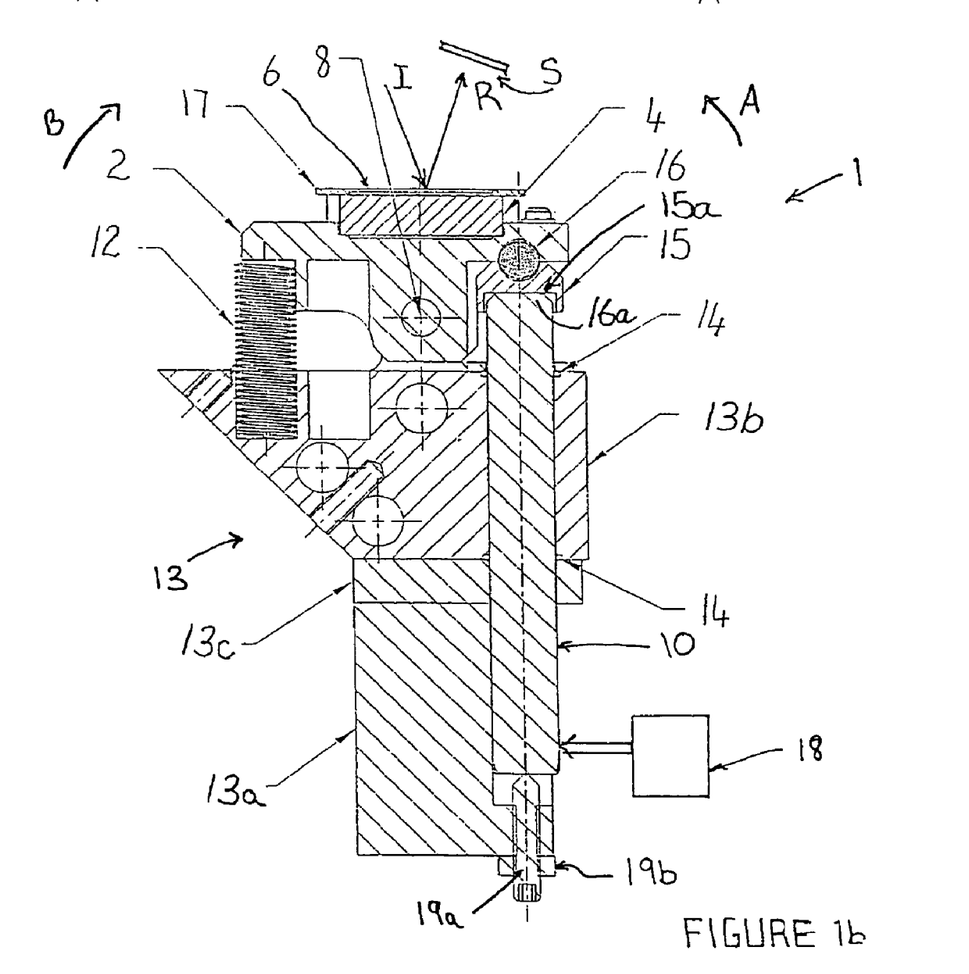

In FIGS. 1a and 1b, there is shown an optical scanning device 1 that is able to reflect an incident optical beam I so that the reflected optical beam R can be directed to a surface S such that the reflected optical beam R is scanned over the surface S.

The optical scanning device 1 comprises a platform 2, a mirror 4 having a reflective surface 6, a pivot 8 about which the platform 2 is able to pivot, a piezoelectric stack actuator 10 to pivot the platform 2 about the pivot 8 in a first direction, and a resilient spring 12 to bias the platform 2 about the pivot 8 in a second direction that is opposed to the first direction. The pivot 8 is a pivot shaft.

The optical scanning device 1 is further provided with a body 13 to support the other components of the optical scanning device 1. The body 13 comprises an anchor block 13a and a main block 13b that are separated by a spacer 13c. The main block 13b supports the piezoelectric stack actuator 10. A pair of O rings 14 are provided around the piezoelectric stack actuator 10 at the locations where the piezoelectric stack actuator 10 extends out of the main block 13b. A cap 15 of low friction material, such as, for example, Teflon, is provided at the end of the piezoelectric stack actuator 10 that is adjacent the platform 2. The cap 15 and the underside of the platform 2 are provided with recesses which accommodate a ball bearing 16. The piezoelectric stack actuator 10 thus acts on the underside of the platform 2 via the cap 15 and the ball bearing 16. The cap 15 is provided with a recess 15a which receives and covers the end 16a of the piezoelectric stack actuator 10. The cap 15 prevents sideways movement of the piezoelectric stack actuator 10 when it acts on the platform 2. A retainer 17 is provided around the mirror 4 to retain the mirror 4 in place.

A push-pull amplifier 18 is provided to drive the piezoelectric stack actuator 10. An adjustment screw 19 and locking nut 19b are provided to adjust the mid position of the scan range of the optical scanning device 1.

Voltage can be applied to the piezoelectric stack actuator 10 to expand the piezoelectric stack actuator 10. The piezoelectric stack actuator 10 acts on the platform 2 at a location in proximity to the pivot 8. For example, the piezoelectric stack actuator 10 may act on the platform 2 at a location that is spaced substantially 5 to 15 mm from the pivot 8. Expansion of the piezoelectric stack actuator 10 pushes on the platform 2 to cause the platform 2 to pivot about the pivot 8 in the direction shown by arrow A in FIG. 1. The spring 12 acts to bias the platform 2 about the pivot 8 in a second direction, shown by arrow B in FIG. 1, that is opposed to the first direction (shown by arrow A). Thus, when a voltage is applied to the piezoelectric stack actuator 10, the piezoelectric stack actuator 10 acts against the spring 12 to pivot the platform 2 in the direction shown by arrow A. Once the applied voltage is removed from the piezoelectric stack actuator 10, the spring 12 returns the platform 2 to its original position. If the applied voltage is reduced, rather than removed completely, the spring 12 biases the platform 2 in the second direction, shown by arrow B in FIG. 1, by an amount corresponding to the reduction in the applied voltage. If the applied voltage to the piezoelectric stack actuator 10 is increased, the piezoelectric stack actuator 10 further expands to cause the platform 2 to pivot about pivot 8 by a further amount corresponding to the increase in the applied voltage.

The spring 12 may be arranged, as required, to bias the platform 2 in a direction opposed to the direction in which the platform 2 is pivoted by the piezoelectric stack actuator 10. The spring 12 may be compressively or expandibly resilient, as required to provide the biasing action to the platform 2 in a direction opposed to the direction in which the piezoelectric actuator 10 acts on the platform 2.

The optical scanning device 1 is able to scan the reflected optical beam R in a first dimension or plane.

The embodiment of the optical scanning device 1 hereinbefore described and illustrated in FIGS. 1a and 1b is arranged such that the piezoelectric stack actuator 10 acts on the platform 2 to push against the platform 2. However, alternatively the scanning device 1 may be arranged such that the piezoelectric stack actuator 10 acts on the platform 2 to pull the platform 2. In such an arrangement, the ball bearing 16 would be fixed to the platform 2 and the cap 15, which would also be fixed to the end 16a of the piezoelectric stack actuator 10. In that way, when a voltage is applied to the piezoelectric stack actuator 10, it would pull the platform 2 in the direction shown by arrow B in FIG. 1. Correspondingly, the spring 12, in such an arrangement, would act to bias the platform 2 about the pivot 8 in the direction shown by arrow A in FIG. 1.

For given scan patterns of an optical beam, such as a laser beam, over a surface S, a relationship exists between the voltage applied to the piezoelectric stack actuator 10 and the pivot position of the platform 2, and mirror 4, (also referred to as the "scanning device position" or "scanner position") and consequently the target, or incident, location of the reflected optical beam R on the surface S.

The scan patterns have steps between each location that vary in distance and direction in a quasi random fashion. The steps in the scan patterns equate to different incident locations of the beam R on the surface S and correspondingly different scanning device positions. The variation of the steps in the scan pattern in a quasi random fashion is achieved by corresponding quasi random changes in the voltage applied to the piezoelectric stack actuator 10. This is in contrast to a regular scan pattern which uses systematic, i.e. non random changes, in the applied voltage. The reason that a quasi random variation is used is that a different shape is being sculpted each time the scanning device 1 is used and there is a need to move the laser beam across the surface being processed so that consecutive laser beam pulses do not overlap and thermal loading is spread across both the surface and time. There may also be a need to adjust the scan pattern to compensate for movements of the surface being treated that may occur.

For a given voltage applied to the piezoelectric stack actuator 10, the position of the platform 2 may vary by 10% of the full range of movement due to hystersis occurring in the piezoelectric stack actuator 10, however, the resultant locations are nevertheless reproducible. The positions of the platform 2 corresponding to these locations can also be determined and are reproducible. It is thus possible to determine a relationship between the scan pattern signal, i.e. the voltage applied to the piezoelectric stack actuator 10, and the position of the platform 2 such that the voltage applied to the piezoelectric stack actuator 10 can be adjusted in advance. In this way, the piezoelectric stack actuator 10 can pivot the platform 2, and thereby the mirror 4, into the correct required position so that the beam R is incident on the surface S at the required incident location.

Figure 2:
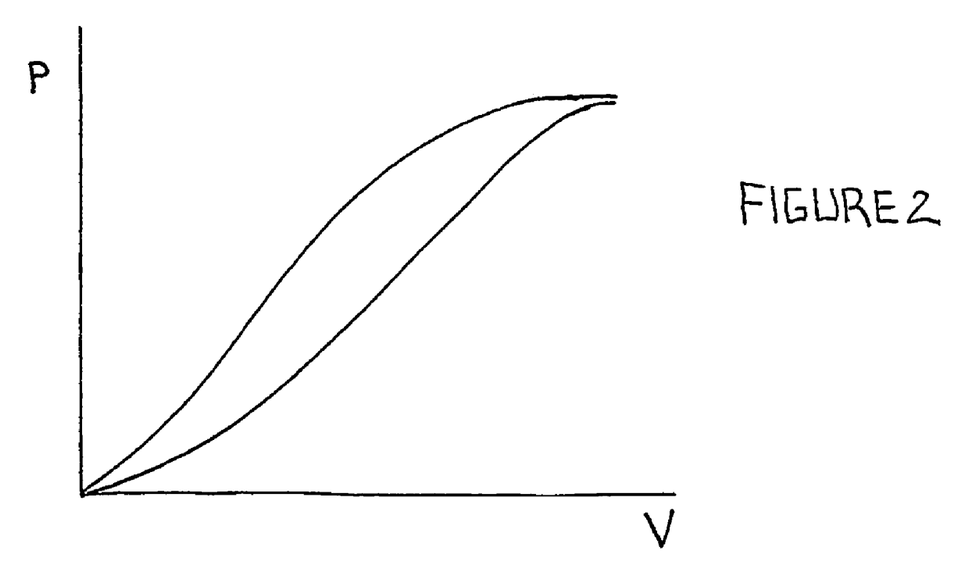
FIG. 2 are plots of the relationship between the position of the platform of the scanning device shown in FIG. 1 versus the corresponding voltage to be applied to the piezoelectric actuator of the scanning device shown in FIG. 1

The relationships between the applied voltage and scanning device position can be determined experimentally for given scan patterns and plotted to produce curves representing the relationships. An example of relationships for scanning device position and voltage applied to the piezoelectric stack actuator 10 is shown in FIG. 2.

The platform 2 of the scanning device 1 may thus be pivoted to the correct position without the need to rely on closed loop feedback. However, the scanning device 1, when used in a closed loop fashion, would also increase the response speed of the scanning device 1 and allow a position sensor to operate as a redundant check of the position of the scanning device 1.

The scanning device 1 may thus be operated as hereinbelow described.

As stated previously herein, for a given current position of the scanning device 1 and a given current voltage applied to the piezoelectric stack actuator 10, the scanning device 1 will follow a predictable path for changes in the applied voltage to the piezoelectric stack actuator 10. These predictable paths are represented by the curves in FIG. 2. The path differs for increases or decreases in the voltage applied to the piezoelectric stack actuator 10 and also depends on the type of piezoelectric device used in the piezoelectric stack actuator 10. These paths are first determined experimentally for a scanning device 1 employing a piezoelectric stack actuator 10 having a particular piezoelectric device.

When it is required to move the incident location of the beam R on the surface S to a new required location, it is determined whether the new required location requires a positive or negative change to the voltage applied to the piezoelectric stack actuator 10 to pivot the platform 2 about the pivot point 8 to a new required position, corresponding to the new required location of the beam R, so that the beam R will strike the surface S at the new required location.

The correct path curve is determined that contains the current scanning device position and applied voltage at the current position of the scanning device. This determination can be made from the relationship between the scanning device position and the applied voltage, which has been previously determined, i.e. as shown in the plot of scanning device position versus applied voltage, as shown in FIG. 2.

This is then used to calculate the new applied voltage required for the new required position of the scanning device. The current scanning device position and the required applied voltage are then recorded for use in determining the voltage to apply to the piezoelectric stack actuator device 10 for the next required position of the scanning device.

If the current position of the scanning device in unknown, e.g. when the scanning device 1 is first switched on, then a voltage of zero can be applied which will produce a fixed position that does not depend on the previous voltage. Effectively, this resets the scanner position to an initial condition.

When a change in the voltage applied to the piezoelectric stack actuator 10 occurs, i.e. a change in the currently applied voltage to the new applied voltage, the voltage changes directly from the currently applied voltage to the new applied voltage, without the applied voltage being returned to zero. However, as an alternative, the voltage may be returned to zero between each change in the applied voltage from the current applied voltage to the new applied voltage.

Figure 3:
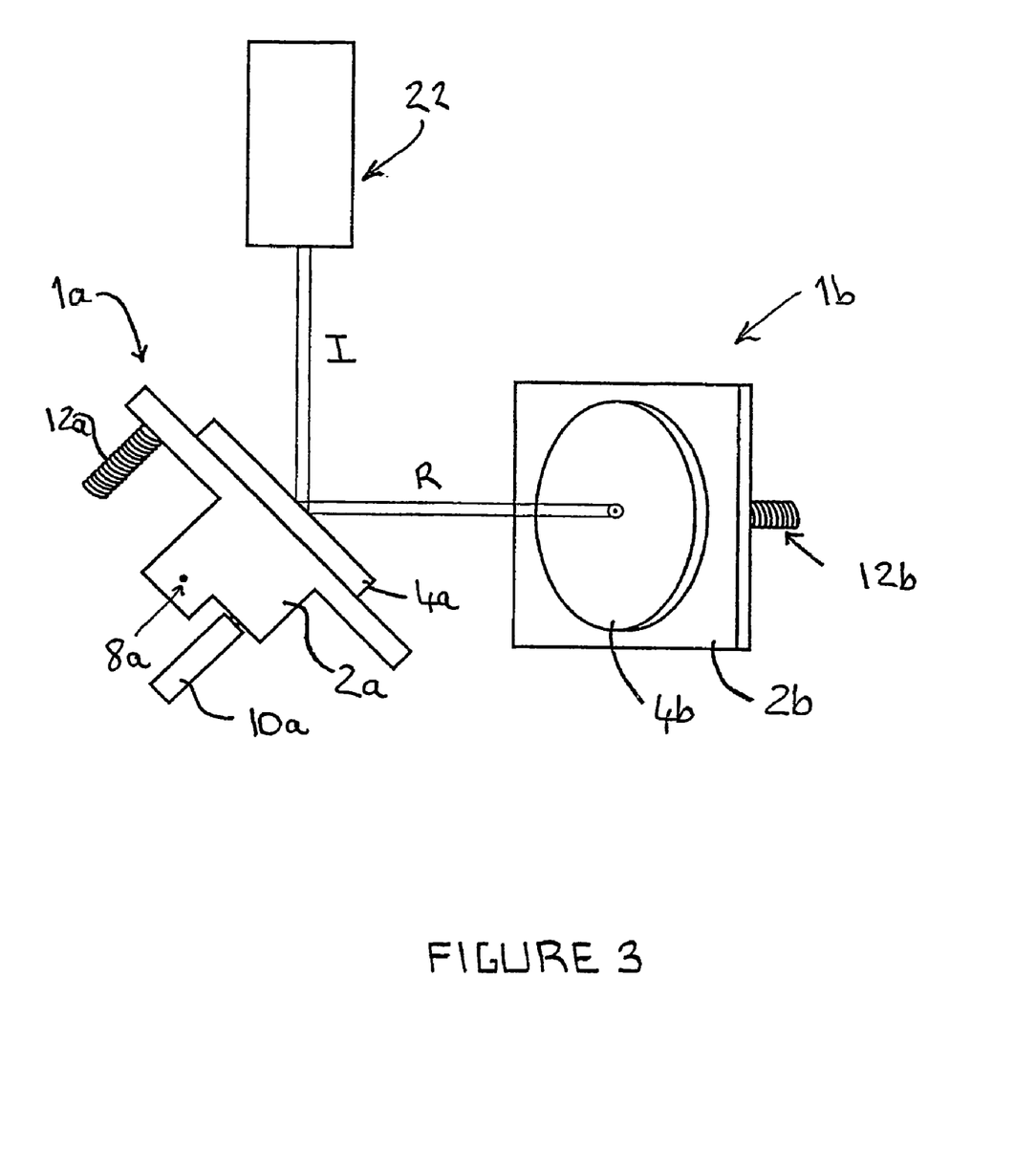
FIG. 3 is a view of an arrangement of two optical scanning devices, of the type shown in FIG. 1, arranged so as to scan an optical beam in two dimensions or planes.

As previously hereinbefore described, the scanning device 1 is able to scan the beam R in a single dimension or plane. In FIG. 3 there is shown a scanning device 1a and scanning device 1b. The scanning devices 1a and 1b are of the same type as the scanning device 1 as previously hereinbefore described with reference to FIGS. 1a and 1b.

The scanning devices 1a and 1b are arranged such that the beam R reflected by the first scanning device 1a can be scanned in a first dimension or plane and is incident upon the mirror 4b of the second optical scanning device 1b. The second optical scanning device 1b is able to reflect the beam R and scan it in a second dimension or plane. The first dimension or plane is substantially orthogonal to the second dimension or plane. In this way, the arrangement of the scanning devices 1a and 1b shown in FIG. 3 can scan the reflected beam in two dimensions or planes that are substantially orthogonal to each other. This enables the reflected beam to be scanned in two dimensions over the surface S.

The piezoelectric stack actuator 10b (obscured in FIG. 3) of the second scanning device 1b pivots the platform 2b about the pivot 8b (obscured in FIG. 3) of the second scanning device 1b in a direction, or about an axis, that is substantially orthogonal to the direction, or about the axis, that the piezoelectric stack actuator 10a pivots the platform 2a of the first scanning device 1a. Similarly, the spring 12b biases the platform 2b about the pivot 8b of the second scanning device 1*b* in a direction, or about an axis, that is substantially orthogonal to the direction, or about the axis, that the spring 12*a* biases the platform 2*a* about the pivot 8*a* of the first scanning device 1*a*.

In the arrangement shown in FIG. 3, the first scanning device 1*a* receives an incident beam I from a laser 22 and is able to scan the reflected beam R in the plane of the drawing sheet depicting FIG. 3. This reflected beam R is incident upon the mirror 4*b* of the second scanning device 1*b*. The beam R is reflected by the mirror 4*b* of the second scanning device 1*b* and can be scanned by the second scanning device 1*b* in a plane that is substantially orthogonal to the plane of the drawing sheet depicting FIG. 3, i.e. the beam R is reflected by the mirror 4*b*, in a plane, out of the drawing sheet depicting FIG. 3.

The description of the relationship between the voltage applied to the piezoelectric stack actuator 10 and the pivot position of the platform 2 and the previous description herein of the operation of the scanning device 1 with reference to FIGS. 1*a*, 1*b* and 2 applies to the scanning devices 1*a* and 1*b* shown in FIG. 3. The scanning devices 1*a* and 1*b* operate together to enable the reflected beam R to be scanned in two dimensions or planes.

Figure 4:
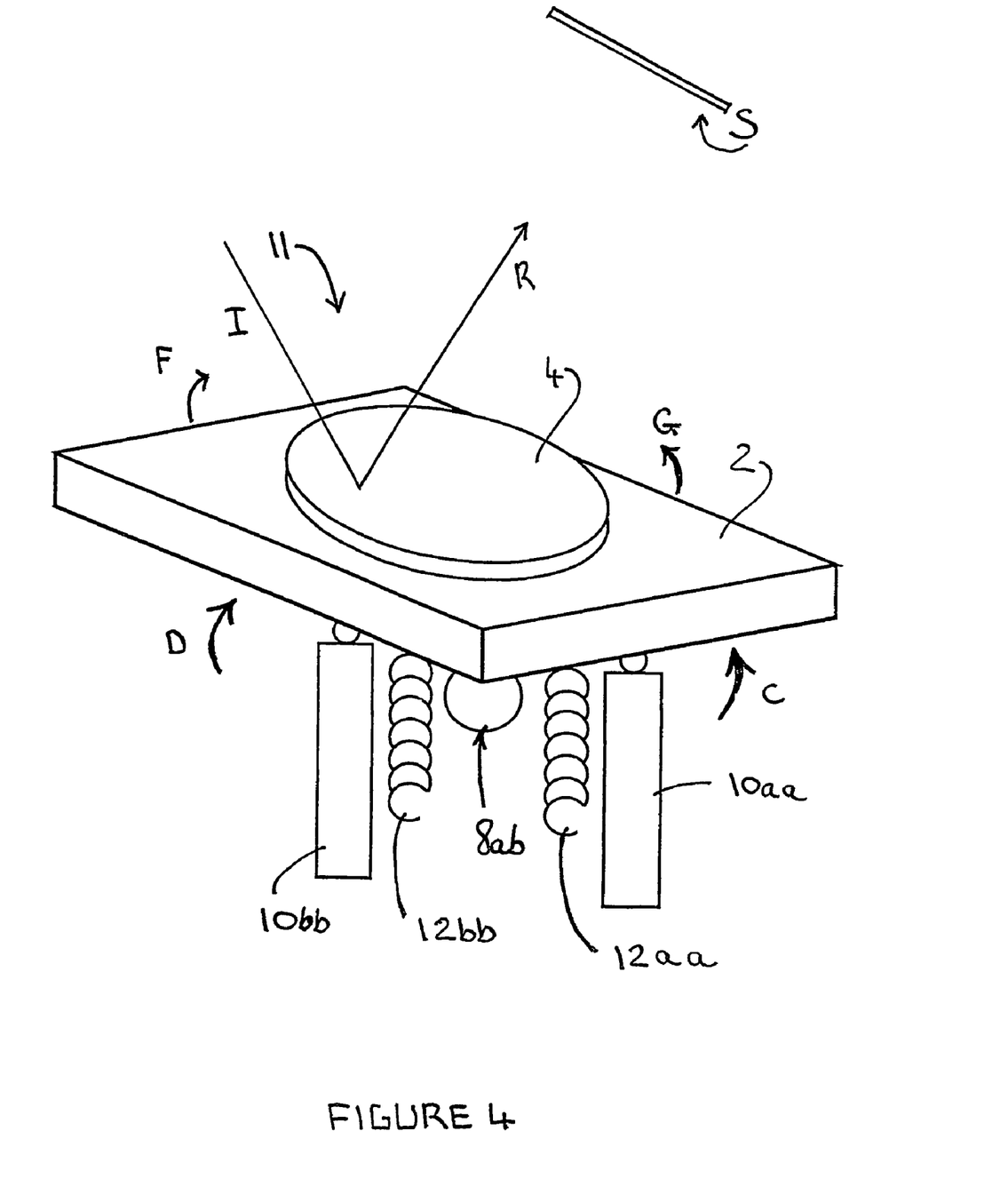
FIG. 4 is a view of a second embodiment of an optical scanning device in accordance with an aspect of the present invention.

In FIG. 4 there is shown a second embodiment of an optical scanning device 11. The optical scanning device 11 is similar to the optical scanning device 1, except that the optical scanning device 11 is provided with a pair of piezoelectric stack actuators 10*aa* and 10*bb* and a pair of resilient springs 12*aa* and 12*bb* and the pivot 8*ab* allows the platform 2 to pivot in at least two directions, or about two axes, that are substantially mutually orthogonal.

The pivot 8*ab* may be provided near a corner of the platform 2. The pivot 8*ab* may be provided as a ball that allows the platform 2 to swivel in any direction.

The piezoelectric stack actuators 10*aa* and 10*bb* and the springs 12*aa* and 12*bb* may be provided in proximity to the pivot 8*ab*. The piezoelectric stack actuators 10*aa* and 10*bb* may be provided such that they act on the platform 2 in proximity to the pivot 8*ab*, for example, at a location spaced substantially 5 to 15 mm from the pivot 8*ab*.

The scanning device 11 permits the platform 2 to pivot about two substantially orthogonal dimensions or axes. Thus, the scanning device 11 provides an alternative to using two scanning devices 1*a* and 1*b*, as shown in FIG. 3, to achieve scanning of the beam R about two substantially orthogonal dimensions or axes to enable the reflected beam to be scanned in two dimensions or planes.

Voltage applied to the piezoelectric stack actuator 10*aa* causes the piezoelectric stack actuator 10*aa* to expand. This in turn, causes the platform 2 to pivot about the pivot 8*ab* in a first direction, shown by arrow C in FIG. 4, against the action of the spring 12*aa*. The spring 12*aa* acts to bias the platform 2 about the pivot 8*ab* in a second direction, shown by arrow F in FIG. 4, that is opposed to the direction shown by arrow C. Similarly, voltage applied to the piezoelectric stack actuator 10*bb* causes the piezoelectric stack actuator 10*bb* to expand. This in turn, causes the platform 2 to pivot about the pivot 8*ab* in the direction shown by arrow D in FIG. 1, against the action of the spring 12*bb*. The spring 12*bb* acts to bias the platform 2 about the pivot 8*ab* in a direction, shown by arrow G in FIG. 1, that is opposed to the direction indicated by arrow D. The axes about which the piezoelectric stack actuators 10*aa* and 10*bb* pivot the platform 2 are mutually orthogonal. The piezoelectric stack actuator 10*aa* and spring 12*aa* enable a reflected beam R to be scanned in a first dimension or plane and the piezoelectric stack actuator 10*bb* and spring 12*bb* enable the reflected beam R to be scanned in a second dimension or plane. The first dimension or plane is substantially orthogonal to the second dimension or plane.

In this way, the reflected beam R can be scanned in two dimensions or planes over a surface S.

The description of the relationship between the voltage applied to the piezoelectric stack actuator 10 and the pivot position of the platform 2 and the operation of the scanning device 1, previously hereinbefore described with reference to FIGS. 1 and 2, also applies to the operation of the scanning device 11.

Figure 5:
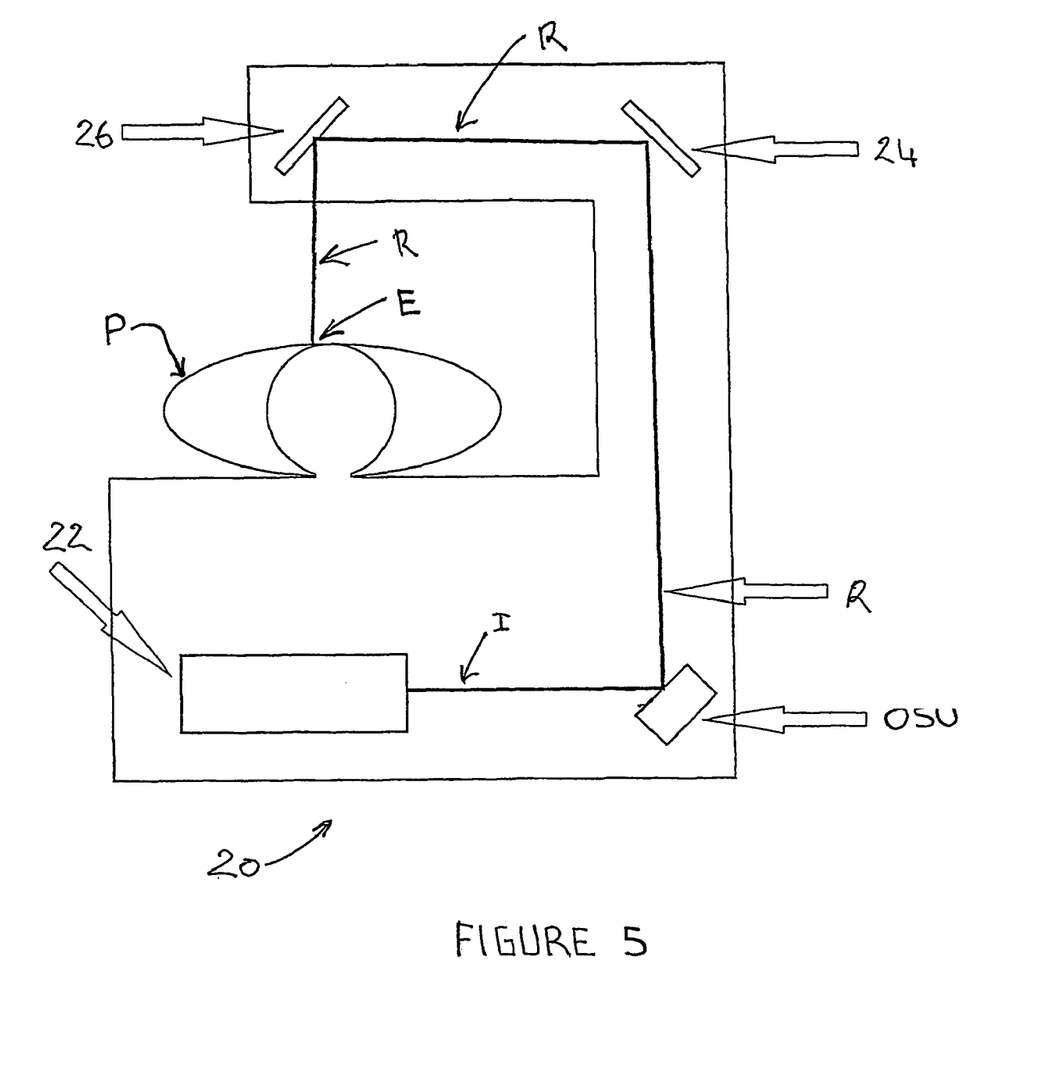
FIG. 5 is a schematic illustration of a refractive surgery laser apparatus in accordance with another aspect of the present invention.

In FIG. 5 there is shown a refractive eye surgery laser apparatus 20.

The refractive eye surgery laser apparatus 20 comprises an optical scanning unit ("OSU"), a laser 22 and first and second mirrors 24 and 26, respectively.

The OSU may be either an arrangement of two scanning devices 1*a* and 1*b*, as shown in FIG. 3, or a scanning device 11 as shown in FIG. 4. In this way, the OSU is able to reflect an incident beam I so that the reflected beam R can be scanned in two dimensions or planes.

The laser 22 emits the laser beam I which is directed to the mirrors 4*aa* and 4*bb*, or mirror 4, of the OSU. The mirrors 4*aa* and 4*bb*, or mirror 4, reflects the incident beam I as reflected beam R.

The reflected beam R is reflected by the mirrors 4*aa* and 4*bb*, or mirror 4, of the OSU to a mirror 24. The mirror 24, in turn, reflects the beam R to a second mirror 26. The mirror 26 reflects the beam R and directs it to the surface to be treated, in this case being the eye E of a patient P.

The OSU is operated, in the manner hereinbefore described with reference to the scanning device 1 and FIGS. 1 and 2, to scan the beam R over the surface of the eye E in the required scan pattern to carry out refractive surgery on the eye E using the laser beam R.

The pivotal movement of the platforms 2*a* and 2*b*, or the platform 2, of the OSU about the pivots 8*a* and 8*b*, or the pivot 8*ab*, causes the path of the reflected beam R to change with changes in the OSU position. The changes in the path of the reflected beam R are preserved by the mirrors 24 and 26. In this way, the path of the beam R that is reflected from the surface 26 changes. These changes correspond to the changes of the OSU. In this way, the beam R reflected by the mirror 26 can be scanned over the eye E to the required locations where refractive surgery is carried out by the beam R.

To achieve the required scan range for the beam R reflected from the mirror 26 to scan the eye E of a patient P, the optical path between the OSU and the eye E is arranged such that it is substantially one metre or more. That is to say, the distance travelled by the beam R from the OSU to the mirror 24, from the mirror 24 to the mirror 26 and from the mirror 26 to the eye E is substantially one metre or more. It is to be understood that by "substantially one metre or more" it is meant that distances of slightly less than one metre, as well as distances of one metre or more, are suitable. This distance enables the refractive laser surgery apparatus 20, employing the OSU, to scan the range required to perform surgery on the eye E.

The refractive eye surgery laser apparatus 20, hereinbefore described, provides an advantage in processing a material, such as corneal tissue of the eye, that may move or may not be exactly the same distance from the laser system each time that the laser 22 is operated to emit a beam I. In that regard, in the OSU, employing a piezoelectrically driven actuator 10, the scan angle, i.e. the angle through which the beam R passes to scan the eye E from one extremity to the other, is much smaller than in prior art systems. Therefore, vertical movements or misalignments of the eye E during surgery will have a much smaller adverse effect on the surgical result compared to prior art galvanometric scanning systems.

Whilst the scanning device of the present invention has been exemplified by its use in a refractive surgery laser system, it may be used in other laser apparatus in which a material is processed by a laser beam.

Modifications and variations such as would be apparent to a skilled addressee are deemed to be within the scope of the present invention.

Throughout the specification, unless the context requires otherwise, the word "comprise" or variations such as "comprises" or "comprising", will be understood to imply the inclusion of a stated integer or group of integers but not the exclusion of any other integer or group of integers.

The invention claimed is:

1. An optical scanning device for use in performing refractive eye surgery on a patient, characterised in that the device comprises:
    a platform,
    a mirror provided on said platform to reflect an optical beam incident on said mirror,
    a pivot about which said platform is able to pivot,
    at least first piezoelectric actuator means to act on said platform to pivot said platform about said pivot in a first direction,
    at least first resilient means to bias said platform about said pivot in a second direction opposed to said first direction,
    drive means to apply a quasi random voltage to said first piezoelectric actuator means to drive said first piezoelectric actuator means,
    wherein said first piezoelectric actuator means acts on said platform at a location in proximity to said pivot, to pivot said platform such that the angle at which said beam is reflected by said mirror is altered to alter the path of the reflected beam to thereby scan the reflected beam in a quasi random fashion in a first plane over a surface.

2. An optical scanning device according to claim 1, characterised in that it further comprises:
    second piezoelectric actuator means to act on said platform to pivot said platform about said pivot in a third direction,
    second resilient means to bias said platform about said pivot in a fourth direction opposed to said third direction, and
    drive means to apply a quasi random voltage to said second piezoelectric actuator means top drive said second piezoelectric actuator means,
    wherein said second piezoelectric actuator means acts on said platform at a location in proximity to said pivot, to pivot said platform such that the angle at which said beam is reflected by said mirror is altered to alter the path of the reflected beam to thereby scan the reflected beam in a quasi random fashion in a second plane over said surface, such that said reflected beam is scannable over said surface in two dimensions.

3. A laser apparatus characterised in that it comprises:
    a laser to emit an optical beam, and
    an optical scanning device according to claim 1,
    wherein the reflected beam is scannable over the surface to perform material processing of said surface by the reflected beam and the optical path of the reflected beam from said optical scanning device to said surface is substantially one metre or more in length.

4. An optical scanning device according to claim 1, characterised in that a cap is provided over an end of said first piezoelectric actuator means that is located proximate said platform to limit sideways movement of said first piezoelectric actuator means proximate said platform.

5. An optical scanning device according to claim 1, characterised in that the drive means to drive said first piezoelectric actuator means is a push-pull amplifier.

6. An optical scanning device according to claim 1, characterised in that said first piezoelectric actuator means acts on said platform to push said platform and said first resilient means is compressively resilient.

7. An optical scanning device according to claim 1, characterised in that said first piezoelectric actuator means acts on said platform to push said platform and said first resilient means is expandably resilient.

8. An optical scanning device according to claim 1, characterised in that said first piezoelectric actuator means acts on said platform to pull said platform and said first resilient means is compressively resilient.

9. An optical scanning device according to claim 1, characterised in that said first piezoelectric actuator means acts on said platform to pull said platform and said first resilient means is expandably resilient.

10. An optical scanning device according to claim 2, characterised in that a cap is provided over an end of said second piezoelectric actuator means that is located proximate said platform to limit sideways movement of said second piezoelectric actuator means proximate said platform.

11. An optical scanning device according to claim 2, characterised in that the drive means to drive said second piezoelectric actuator means is a push-pull amplifier.

12. An optical scanning device according to claim 2, characterised in that said second piezoelectric actuator means acts on said platform to push said platform and said second resilient means is compressively resilient.

13. An optical scanning device according to claim 2, charactensed in that said second piezoelectric actuator means acts on said platform to push said platform and said second resilient means is expandably resilient.

14. An optical scanning device according to claim 2, characterised in that said second piezoelectric actuator means acts on said platform to pull said platform and said second resilient means is compressively resilient.

15. An optical scanning device according to claim 2, characterised in that said second piezoelectric actuator means acts on said platform to pull said platform and said second resilient means is expandably resilient.

16. An optical scanning device according to claim 1, characterised in that said optical beam is a laser beam.

17. An optical scanning device according to claim 1, characterised in that said first plane and said second plane are substantially mutually orthogonal.

18. An optical scanning apparatus for use in performing refractive eye surgery on a patient, characterised in that the apparatus comprises:
    a first optical scanning device,
    and a second optical scanning device,
    said first optical scanning device comprising
        a first platform
        a first mirror provided on said first platform to reflect an optical beam incident on said first mirror,
        a first pivot about which said first platform is able to pivot, first piezoelectric actuator means to act on said first
platform to pivot said first platform about
said first pivot in a first direction, and
first resilient means to bias said first platform about said
first pivot in a second direction opposed to said first
direction, and
first drive means to apply a quasi random voltage to
said first piezoelectric actuator means to drive said
first piezoelectric actuator means; and
said second optical scanning device comprising
a second platform
a second mirror provided on said second platform to
reflect the optical beam incident on said second
mirror,
a second pivot about which said second platform is able
to pivot,
second piezoelectric actuator means to act on said
second platform to pivot said second platform about
said second pivot in a third direction, and
second resilient means to bias said second platform
about said second pivot in a fourth direction opposed
to said third direction, and
second drive means to apply a quasi random voltage to
said second piezoelectric actuator means to drive
said second piezoelectric actuator means,
wherein said first piezoelectric actuator means acts on
said first platform at a location in proximity to said first
pivot to pivot said first platform such that the angle at
which said beam is reflected by said first mirror is
altered to alter the path of the reflected beam to thereby
scan the reflected beam in a quasi random fashion in a
first plane, and said second optical scanning device is
arranged such that said second mirror receives said
beam reflected by said first mirror and said second
piezoelectric actuator means acts on said second platform at a location in proximity to said second pivot to
pivot said second platform such that the angle at which
said beam is reflected by said second mirror is altered
to alter the path of the reflected beam to thereby scan
the reflected beam in a quasi random fashion in a
second plane, such that said reflected beam 5 is scannable over said surface in two dimensions.

19. An optical scanning apparatus according to claim 18, characterised in that a cap is provided over an end of said first piezoelectric actuator means that is located proximate said first platform to limit sideways movement of said first piezoelectric actuator means proximate said first platform.

20. An optical scanning apparatus according to claim 18, characterised in that the first drive means to drive said first piezoelectric actuator means is a first push-pull amplifier.

21. An optical scanning apparatus according to claim 18, characterised in that said first piezoelectric actuator means acts on said first platform to push said first platform and said first resilient means is compressively resilient.

22. An optical scanning apparatus according to claim 18, characterised in that said first piezoelectric actuator means acts on said first platform to push said first platform and said first resilient means is expandably resilient.

23. An optical scanning apparatus according to claim 18, characterised in that said first piezoelectric actuator means acts on said first platform to pull said first platform and said first resilient means is compressively resilient.

24. An optical scanning apparatus according to claim 18, characterised in that said first piezoelectric actuator means acts on said first platform to pull said first platform and said first resilient means is expandably resilient.

25. An optical scanning apparatus according to claim 18, characterised in that a cap is provided over an end of said second piezoelectric actuator means that is located proximate said second platform to limit sideways movement of said second piezoelectric actuator means proximate said second platform.

26. An optical scanning apparatus according to claim 18, characterised in that the second drive means to drive said second piezoelectric actuator means is a second push-pull amplifier.

27. An optical scanning apparatus according to claim 18, characterised in that said second piezoelectric actuator means acts on said second platform to push said second platform and said second resilient means is compressively resilient.

28. An optical scanning apparatus according to claim 18, characterised in that said second piezoelectric actuator means acts on said second platform to push said second platform and said second resilient means is expandably resilient.

29. An optical scanning apparatus according to claim 18, characterised in that said second piezoelectric actuator means acts on said second platform to pull said second platform and said second resilient means is compressively resilient.

30. An optical scanning apparatus according to claim 18, characterised in that said second piezoelectric actuator means acts on said second platform to pull said second platform and said second resilient means is expandably resilient.

31. An optical scanning apparatus according to claim 18, characterised in that said optical beam is a laser beam.

32. An optical scanning apparatus according to claim 18, characterised in that said first plane and said second plane are substantially mutually orthogonal.

33. A laser apparatus comprising:
a laser to emit an optical beam, and
an optical scanning apparatus according to claim 18,
wherein the reflected beam is scannable over a surface to perform material processing of said surface by the reflected beam and the optical path of the reflected beam from said second optical scanning device to the said surface is substantially one metre or more in length.

34. A laser apparatus for use in performing refractive eye surgery on a patient, characterised in that the apparatus comprises:
a laser to emit an optical beam, and
an optical scanning device comprising
a platform,
a mirror provided on said platform to reflect a said optical beam incident on said mirror,
a pivot about which said platform is able to pivot,
first piezoelectric actuator means to act on said platform to pivot said platform about said pivot in a first direction,
first resilient means to bias said platform about said pivot in a second direction opposed to said first direction,
first drive means to apply a quasi random voltage to said first piezoelectric actuator means to drive said first piezoelectric actuator means,
second piezoelectric actuator means to act on said platform to pivot said platform about said pivot in a third direction, second resilient means to bias said platform about- said pivot in a fourth direction opposed to said third direction, second drive means to apply a quasi random voltage to said second piezoelectric actuator means to drive said second piezoelectric actuator means, wherein said first piezoelectric actuator means acts on said platform at a location in proximity to said pivot, to pivot said platform such that the angle at which said beam is reflected by said mirror is altered to alter the path of the reflected beam to thereby scan the reflected beam in a quasi random fashion in a first plane and said second piezoelectric actuator means acts on said platform at a location in proximity to said pivot, to pivot said platform such that angle at which said beam is reflected by said mirror is altered to alter the path of the reflected beam to thereby scan the reflected beam in a quasi random fashion in a second plane, such that said reflected beam is scannable over said surface in two dimensions to thereby scan the reflected beam over the surface to perform material processing of said surface by the reflected beam and the optical path of the reflected beam from said optical scanning device to said surface is substantially one metre or more in length.

35. A laser apparatus according to claim 34, characterised in that it further comprises a second mirror to reflect the reflected beam reflected by said mirror of said optical scanning device prior to said reflected beam being reflected to said surface.

36. A laser apparatus according to claim 35, characterised in that it further comprises a third mirror to receive the reflected beam from said second mirror and said third mirror is arranged to reflect said beam to said surface.

37. A laser apparatus according to claim 34, characterised in that said laser apparatus is a refractive eye surgery laser apparatus, and the surface on which the material processing is performed by the reflected beam is the eye of a patient on which the refractive surgery is performed by the reflected beam.

38. A laser apparatus for use in performing refractive eye surgery on a patient, comprising:
   a laser to emit an optical beam,
   a first optical scanning device, and
   a second optical scanning device,
   said first optical scanning device comprising
      a first platform
      a first mirror provided on said first platform to reflect an optical beam incident on said first mirror,
      a first pivot about which said first platform is able to pivot,
      first piezoelectric actuator means to act on said first platform to pivot said first platform about said first pivot in a first direction, and
      first resilient means to bias said first platform about said first pivot in a second direction opposed to said first direction, and
      first drive means to apply a quasi random voltage to said first piezoelectric actuator means to drive said first piezoelectric actuator, and
   said second optical scanning device comprising
      a second platform
      a second mirror provided on said second platform to reflect the optical beam incident on said second mirror,
      a second pivot about which said second platform is able to pivot,
      second piezoelectric actuator means to act on said second platform to pivot said second platform about said second pivot in a third direction, and
      second resilient means to bias said second platform about said second pivot in a fourth direction opposed to said third direction, and
      second drive means to apply a quasi random voltage to said second piezoelectric actuator means to drive said second piezoelectric actuator means,
   wherein said first piezoelectric actuator means acts on said first platform at a location in proximity to said first pivot to pivot said first platform such that the angle at which said beam is reflected by said first mirror is altered to alter the path of the reflected beam to thereby scan the reflected beam in a quasi random fashion in a first plane, and said second optical scanning device is arranged such that said second mirror receives said beam reflected by said first mirror and said second piezoelectric actuator means acts on said second platform at a location in proximity to said second pivot to pivot said second platform such that the angle at which said beam is reflected by said second mirror is altered to alter the path of the reflected beam to thereby scan the reflected beam in a quasi random fashion in a second plane, such that said reflected beam is scannable over said surface in two dimensions to thereby scan the reflected beam over a surface to perform material processing of said surface by the reflected beam and the optical path of the reflected beam from said second optical scanning device to the said surface is substantially one metre or more in length.

39. A laser apparatus according to claim 38, characterised in that a third mirror is provided to reflect the reflected beam reflected by said second mirror prior to said reflected beam being reflected to said surface.

40. A laser apparatus according to claim 39, characterised in that a fourth mirror is provided to receive the reflected beam from said third mirror and said fourth mirror is arranged to reflect said reflected beam to said surface.

41. A method of scanning an optical beam, in at least a first plane, over a surface using an optical scanning device according to claim 1, characterised in that it comprises
   determining a required location for the optical beam to be incident on said surface, determining whether a positive or negative change to the voltage applied to a said piezoelectric actuator means is required to pivot said platform to a required position corresponding to the said required location, comparing the existing position of said platform and the voltage applied to said piezoelectric actuator means with the required position of said platform,
   calculating the required voltage to be applied to said piezoelectric actuator means corresponding to the required position of said platform,
   applying the said required voltage to said piezoelectric actuator means to move said platform to said required position such that the optical beam is incident on said surface at the said required location.

42. A method according to claim 41, characterised in that said required position of said platform and the corresponding required voltage to be applied to said piezoelectric actuator means are recorded for use in determining the voltage to be applied to said piezoelectric actuator means for the next location at which said optical beam is to be incident on said surface.

43. A method according to claim 41, characterised in that the steps of the method as cariled out on each of the first piezoelectric actuator means and the second piezoelectric actuator means to pivot said platform to the required position for the optical beam to be incident on said surface at said required location, to thereby scan the optical beam in two planes, such that the optical beam is scannable in two dimensions over said surface.

44. A method of scanning an optical beam, in two planes, over a surface using an optical scanning apparatus according to claim 41, characterised in that it comprises determining a required location for the optical beam to be incident on said surface, determining whether a positive or negative change to the voltage applied to each of said first piezoelectric actuator means and said second piezoelectric is required to pivot each said platform to a required position corresponding to the said required location, comparing the existing position of each said platform and the voltage applied to said first piezoelectric actuator means and said second piezoelectric means, respectively, with the required position of each said platform, calculating the required voltage to be applied to said first piezoelectric actuator means and said second piezoelectric means, respectively, corresponding to the required position of each respective said platform, applying the said required voltage to said first piezoelectric actuator means and said second piezoelectric actuator means, respectively, to move each said platform to the respective said required position such that the optical beam is incident at the said required location.

45. A method according to claim 44, characterised in that said required position of each said platform and the corresponding required voltage to be applied to said first piezoelectric actuator means and said second piezoelectric actuator means, respectively, are recorded for use in determining the voltage to be applied to said first piezoelectric actuator means and said second piezoelectric actuator means, respectively, for the next location at which said optical beam is to be incident on said surface.

* * * * *